(12) United States Patent
Allen

(10) Patent No.: US 8,701,246 B2
(45) Date of Patent: Apr. 22, 2014

(54) REMOVABLE GROMMET DEVICE AND METHOD OF USING THEREOF

(75) Inventor: Kraig Herman Allen, Leesburg, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 0 days.

(21) Appl. No.: 13/614,185

(22) Filed: Sep. 13, 2012

(65) Prior Publication Data

US 2013/0064709 A1     Mar. 14, 2013

Related U.S. Application Data

(60) Provisional application No. 61/534,647, filed on Sep. 14, 2011.

(51) Int. Cl.
*F16L 5/00* (2006.01)

(52) U.S. Cl.
USPC .......................... 16/2.1; 248/56; 248/346.04

(58) Field of Classification Search
USPC ................ 16/2.1–2.5; 174/152 G, 153 G; 248/346.04, 56; 422/243, 300; 277/606, 616

See application file for complete search history.

(56) References Cited

U.S. PATENT DOCUMENTS

| | | | |
|---|---|---|---|
| 1,483,218 A * | 2/1924 | Fahnestock | 174/153 G |
| 2,438,499 A | 3/1948 | Hartman | |
| 2,664,458 A | 12/1953 | Rapata | |
| 2,858,150 A * | 10/1958 | Neher et al. | 277/564 |
| 3,110,337 A | 11/1963 | Biesecker | |
| 3,213,189 A * | 10/1965 | Mitchell et al. | 174/138 R |
| 3,217,584 A | 11/1965 | Amesbury | |
| 3,309,955 A | 3/1967 | Turnbull et al. | |
| 3,611,861 A | 10/1971 | Schulze | |
| 3,651,734 A | 3/1972 | McSherry | |
| 3,665,548 A * | 5/1972 | Mason | 174/153 G |
| 3,678,797 A | 7/1972 | Seckerson | |
| 3,788,655 A * | 1/1974 | Hathaway | 277/637 |
| 3,964,364 A | 6/1976 | Pie | |
| 4,136,599 A | 1/1979 | Hammer, Jr. | |
| 4,276,806 A | 7/1981 | Morel | |
| 4,299,363 A * | 11/1981 | Datschefski | 248/56 |
| 4,843,675 A | 7/1989 | Diamantis | |
| 5,518,115 A | 5/1996 | Latulippe | |
| 5,525,314 A | 6/1996 | Hurson | |
| 5,537,714 A * | 7/1996 | Lynch et al. | 16/2.1 |
| 5,645,282 A | 7/1997 | Belter | |
| 5,775,859 A | 7/1998 | Anscher | |
| 5,975,820 A | 11/1999 | Kirchen | |
| 6,099,812 A | 8/2000 | Allen et al. | |
| 6,364,586 B1 | 4/2002 | Okada | |

(Continued)

*Primary Examiner* — William Miller
(74) *Attorney, Agent, or Firm* — Hayes Soloway PC

(57) ABSTRACT

A grommet device and method of using a grommet device is provided. A top structure has a top surface. An aperture having a central axis is positioned interior of the top structure. A sidewall is formed around the aperture and connected to the top structure. The sidewall is positioned substantially perpendicular from the top surface of the top structure. At least two upper protruding structures are connected to the top structure at different locations along the top structure, wherein each of the upper protruding structures extends into the aperture. At least two lower protruding structures extend from the sidewall at different locations along the sidewall, wherein each of the lower protruding structures have a flexing portion extending into the aperture, wherein each of the upper protruding structures are substantially radially aligned with the flexing portion of each of the lower protruding structures, respectively.

13 Claims, 5 Drawing Sheets

(56) References Cited

U.S. PATENT DOCUMENTS

| | | |
|---|---|---|
| 6,382,575 B1 | 5/2002 | Frush et al. |
| 6,505,386 B1 | 1/2003 | Allie |
| 6,514,023 B2 | 2/2003 | Moerke |
| 6,854,946 B2 | 2/2005 | Bauer |
| 7,579,556 B2 * | 8/2009 | Tapper .......... 174/650 |
| 7,579,557 B2 * | 8/2009 | Tapper .......... 174/650 |
| 7,582,836 B2 * | 9/2009 | Tapper .......... 174/650 |
| 2006/0261695 A1 | 11/2006 | Terrill et al. |
| 2007/0138042 A1 | 6/2007 | Wood |
| 2007/0205123 A1 | 9/2007 | Bettenhausen et al. |
| 2010/0065456 A1 | 3/2010 | Junk et al. |
| 2011/0014005 A1 | 1/2011 | Shinozaki |
| 2011/0091301 A1 | 4/2011 | Shimizu et al. |
| 2011/0170982 A1 | 7/2011 | Watanabe |
| 2011/0197405 A1 | 8/2011 | Kato et al. |
| 2013/0064734 A1 * | 3/2013 | Allen .......... 422/300 |

* cited by examiner

REMOVABLE GROMMET DEVICE AND METHOD OF USING THEREOF

CROSS REFERENCE TO RELATED APPLICATION

This application claims benefit of U.S. Provisional Application Ser. No. 61/534,647, entitled, "Removable Grommet Device with Prongs and Method of Using Thereof" filed Sep. 14, 2011, the entire disclosure of which is incorporated herein by reference.

FIELD OF THE DISCLOSURE

The present disclosure is generally related to grommets and more particularly is related to a removable grommet device and method of using thereof.

BACKGROUND OF THE DISCLOSURE

Within the medical industry, there is a need for holding a variety of medical instruments for various purposes. For example, a surgeon needs to be able to access medical instruments for surgery quickly, a dentist needs to be able to access his or her dental tools, and virtually all medical instruments must be placed within a holder during a sterilization process. Conventional holding containers may include a variety of bases holding insertable trays that have specifically-designed areas for holding specific tools. However, with smaller tools, such as small dental tools, it is frequently inefficient to store them in these containers, since they're prone to being moved around and jostled as the container is moved. This may result in a grouping of smaller tools in one area, which means that the surgeon or medical staff member must sift through the grouping to locate a specific tool.

Conventionally, medical instruments are often held in containers or trays with holes and grommets. The grommets may be positioned within the hole and provide a secure interface between the medical instrument and the hole within the container or tray. Often, the grommets are sized to match a certain shaft size of a medical instrument, and a container or tray may include a variety of different sized grommets, each specifically engineered and designed to hold one of a variety of medical instruments. These medical instruments have varying shaft sizes and it often becomes tedious to search for the appropriately sized grommet that matches a particular shaft size of the medical instrument. It is not uncommon for a medical tray to have fifty or more grommets, with a dozen or more different sizes. Thus, the time it takes to match a specific medical instrument to a specifically sized grommet may result in inefficient use of valuable time.

Most grommets in use today are intended to be permanent fixtures in medical sterilization trays, in that they are not designed to be removed on a regular basis. This is due to the high risk of harboring bacteria and other contaminants within the spaces, crevices and other areas exposed when the grommet is removed from the tray. When the grommets are permanently installed within the holes, the surfaces of the grommets form tight seals with the container or the tray. This may prevent bacterial from becoming lodge within cracks, crevices or other areas, which may prevent complete sterilization of the medical tool. However, users often try and remove the grommets when they become damaged, or when they desire to reposition the grommet in a new location. This removal of the grommet may result in damage to the grommet structure itself, as well as present additional areas for harboring bacterial.

Thus, a heretofore unaddressed need exists in the industry to address the aforementioned deficiencies and inadequacies.

SUMMARY OF THE DISCLOSURE

Embodiments of the present disclosure provide a grommet device. Briefly described, in architecture, one embodiment of the system, among others, can be implemented as follows. A circular top structure has a top surface, wherein an aperture having a central axis is positioned interior of the top structure. A sidewall is formed around the aperture and connected to the circular top structure, wherein the sidewall is positioned substantially perpendicular from the top surface of the circular top structure. At least two upper protruding structures are connected to the circular top structure at different locations along the circular top structure, wherein each of the at least two upper protruding structure extend into the aperture. At least two lower protruding structures extend from the sidewall at different locations along the sidewall, wherein each of the at least two lower protruding structures have a flexing portion extending into the aperture, wherein each the at least two upper protruding structures is substantially radially aligned with the flexing portion of each of the at least two lower protruding structures, respectively.

The present disclosure can also be viewed as providing a medical instrument sterilization device. Briefly described, in architecture, one embodiment of the device, among others, can be implemented as follows. A sterilization platform has a plurality of holes formed therein. A grommet device is positioned within one of the plurality of holes, the grommet device having a top structure abutting a top surface of the sterilization platform and a sidewall connected to the top structure and abutting an inner wall of the hole, wherein an aperture is formed within the top structure. At least two upper protruding structures are connected to the top structure at different locations along the top structure, wherein each of the at least two upper protruding structures extend into the aperture and an upper contact point positioned at an innermost portion of the at least two upper protruding structures. At least two lower protruding structures extend from the sidewall at different locations along the sidewall, wherein each of the at least two lower protruding structures have a flexing portion extending into the aperture and a lower contact point positioned at an innermost portion of the flexing portion of the at least two lower protruding structures. A medical instrument is positioned within the aperture and in contact with all of the upper and lower contact points, wherein the medical instrument is frictionally retained in a substantially stationary position.

The present disclosure can also be viewed as providing a method of sterilizing a medical instrument. In this regard, one embodiment of such a method, among others, can be broadly summarized by the following steps: providing a medical instrument sterilization platform having at least one hole formed therein, wherein a grommet device is positioned within the at least one hole; inserting the medical instrument into an aperture formed within the grommet device, thereby contacting the medical instrument with at least two upper protruding structures and at least two lower protruding structures formed with the grommet device, thereby biasing each of the at least two upper and lower protruding structures radially outwards away from a central axis of the aperture; and retaining the medical instrument within the aperture of the grommet device during a medical instrument sterilization process.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
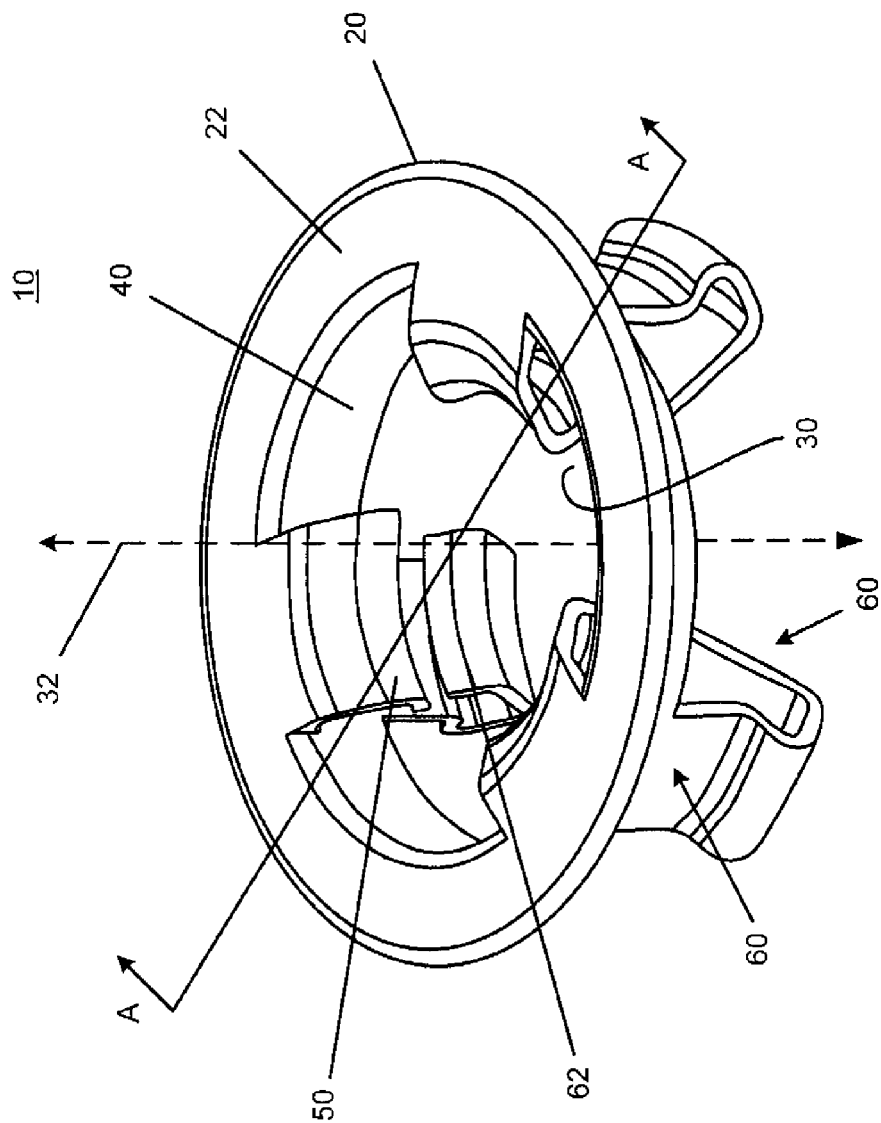
FIG. 1 is a plan view illustration of a grommet device, in accordance with a first exemplary embodiment of the present disclosure.

FIG. 1 is a plan view illustration of a grommet device 10, in accordance with a first exemplary embodiment of the present disclosure. The grommet device 10, which may be referred to as 'device 10,' includes a circular top structure 20 having a top surface 22, wherein an aperture 30 having a central axis 32 is positioned interior of the top structure 20. A sidewall 40 is formed around the aperture 30 and connected to the circular top structure 20, wherein the sidewall 40 is positioned substantially perpendicular from the top surface 22 of the circular top structure 20. At least two upper protruding structures 50 are connected to the circular top structure 20 at different locations along the circular top structure 20, wherein each of the at least two upper protruding structures 50 extend into the aperture 30. At least two lower protruding structures 60 extend from the sidewall 40 at different locations along the sidewall 40, wherein each of the at least two lower protruding structures 60 have a flexing portion 62 extending into the aperture 30, wherein each the at least two upper protruding structures 50 is substantially radially aligned with the flexing portion 62 of each of the at least two lower protruding structures 60, respectively.

The device 10 may be used with medical tool holding structures, such as sterilization trays used for holding medical instruments during a sterilization process. Accordingly, the device 10 may be used in any industry utilizing medical tools, such as tools, instruments, or any other type of implement used for surgical procedures, operations, or other medical procedures. For example, the device 10 may be used to hold medical instruments in surgical environments before, during and/or after a surgical procedure, or a medical instrument sterilization process. Similarly, the device 10 may be used with dental instruments for dental operations, routine cleanings, or for any other use. Other settings and uses within the medical field are also envisioned, all of which are considered within the scope of the present disclosure.

Figure 2:
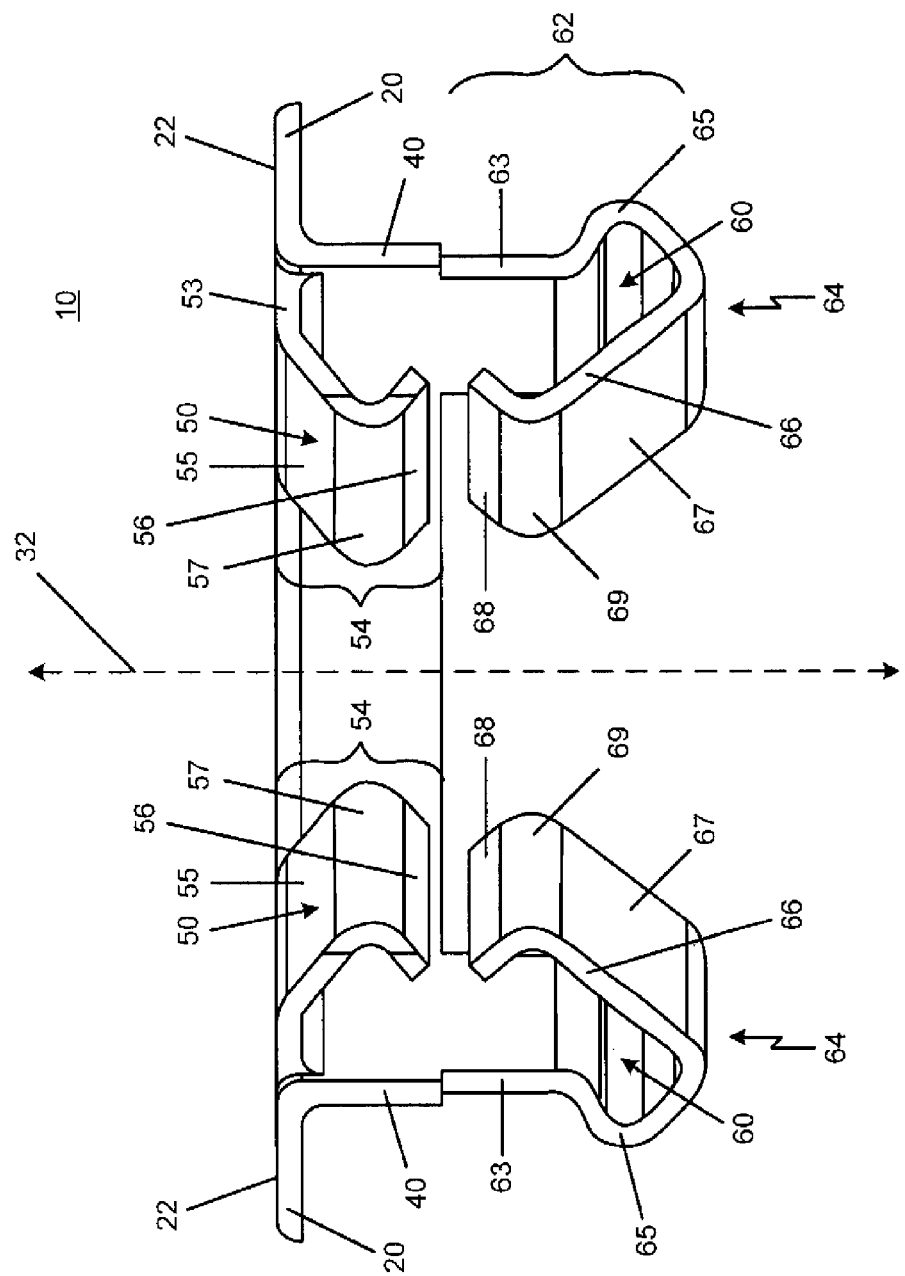
FIG. 2 is a cutout view illustration of the grommet device along the line A-A of FIG. 1, in accordance with the first exemplary embodiment of the present disclosure.

FIG. 2 is a cutout view illustration of the grommet device 10 along the line A-A of FIG. 1, in accordance with the first exemplary embodiment of the present disclosure. As is shown in FIGS. 1-2, the general structure of the device 10 may be formed by the circular top structure 20 and the sidewall 40, with the upper and lower protruding structures 50, 60 extending therefrom. The device 10 is designed for use with a grommet-holding structure, such as a medical sterilization platform with holes to receive the device 10. The medical sterilization platform may commonly include a medical instrument tray with openings, holes, or other structures, which can secure the device 10 in place. When the device 10 is positioned within the medical sterilization platform, the external surface of the sidewall 40 may contact an inner wall of the hole within the medical sterilization platform, and the underside of the circular top structure 20 may contact an upper surface of the medical sterilization platform. In this orientation, the medical sterilization platform may properly support the device 10 and hold it in place for successful use with sterilizing medical instruments.

The sidewall 40 may integrally connect the base structure 20 to the circular top structure 20. The sidewall 40 may commonly have a substantially cylindrical shape that is configured to be positioned within the grommet-holding structure. For example, the sidewall 40 may be positioned abutting the grommet-holding structure, with the circular top structure 20 contacting an upper surface of the grommet-holding structure. As will be discussed, a portion of the lower protruding arm 60 may be positioned opposing the circular top structure 20, with the grommet-holding structure therebetween.

The aperture 30 may be positioned within the device 10, interior of the sidewall 40 and the circular top structure 20. The aperture 30 may be a cavity, a cutout of material, or hole, which is positioned within the device 10, commonly aligned along a central axis 32 of the cylindrical shape of the device 10. This central axis 32 may run through a center point of the grommet-holding structure, or may be positioned off-center, as various designs may dictate. The aperture 30 may be sized to hold any type of medical instrument, and thus, may have any size diameter. The aperture 30 includes an interior space, which may be defined by an interior sidewall of the sidewall 40. The interior space may be characterized as the space within the aperture 30 that is surrounded by any of the circular top structure 20 and the sidewall 40.

The upper and lower protruding structures 50, 60, which may also be known as prongs, tabs, or angled tabs, may each have a shape that allows for flexibility when biased by a force, such as the force from a medical instrument inserted into the aperture 30. For example, as is shown, the top and bottom portions of the upper and lower protruding structures 50, 60 may each include arced or curved surfaces with a number of bends within the structure of the upper and lower protruding structures 50, 60. The various structures may include facing surfaces for contacting the medical instrument, flexing structures that flex under the force of an inserted medical instrument, and connecting structures which provide a connection between upper and lower protruding structures 50, 60 and other components. Also, as one having skills in the art can see, the flexibility of the upper and lower protruding structures 50, 60 may be dependent with or relative to other components.

At least two upper protruding structures 50 and lower protruding structures 60 may be included with the device 10, but any number of upper protruding structures 50 and lower protruding structures 60 may be included. For example, in FIG. 1, there are three upper protruding structures 50 and lower protruding structures 60 depicted. The upper protruding structures 50 and lower protruding structures 60 are formed to be positioned substantially within the aperture 30. The upper protruding structures 50 may be connected to the circular top structure 20 whereas the lower protruding structures 60 may be connected to the sidewall 40.

As is shown in FIG. 2, the upper protruding structures 50 generally include a platform 53 connected to the circular top structure 20 that has an upper surface that is substantially planar with the top surface 22 of the circular top structure 20 and a biasable arm 54 integral with the platform 53, wherein the biasable arm 54 angularly extends towards the central axis 32 from the platform 53. The biasable arm 54 may be characterized as the structure of the upper protruding structure 50 that may flex or bend when contacted by a medical instrument. For example, when a medical instrument is positioned within the aperture 30, the platform 53 is positioned relatively close to the circular top structure 20, and thus may not experience bending, movement, or material stresses. On the other hand, when the medical instrument is inserted into the aperture 30, the biasable arm 54, i.e., the more interior portions of the upper protruding structures 50, may be flexed or bent.

The biasable arm 54 has a general structure that includes first and second arm portions 55, 56 that are angularly connected together to form an upper contact point 57. The upper contact point 57 may substantially face the central axis 32 and the interior of the aperture 30. In use, the upper contact point 57 may interface with the medical instrument, while the first and second arm portions 55, 56 flex or bend relative to the platform 53 and the circular top structure 22. The angular construction of the first and second arm portions 55, 56 may vary greatly, and may often be selected based on the intended size of the medical instrument that the device 10 may hold. The upper contact point 57 may be axially movable between the sidewall 40 and the central axis 32, or in other words, the upper contact point 57 may move in a direction that is in alignment with a radius of the aperture 30. When the medical instrument is positioned within the aperture 30, the upper contact point 57 may be forced away from the central axis 32, and when the medical instrument is removed from the aperture 30, the upper contact point 57 may move towards the central axis 32 to be reoriented to its natural position. The lower most portion of the upper protruding structure 50, namely the lower tip of the second arm 56 may be substantially aligned with a terminating edge of the sidewall 40.

The flexing structures 62 of the lower protruding structures 60 generally comprise an extending platform 63 connected to the sidewall 40 and a biasable arm 64 integral with the extending platform 63. The extending platform 63 may be substantially aligned with the sidewall 40, and the biasable arm 64 may stem from the extending platform 63 with a variety of angles, and structures. For example, the biasable arm 64 may be characterized as having at least a first section 65 and a second section 66, where the first section 65 of the biasable arm 64 is angularly connected to the extending platform 63 and extends outwards from the central axis 32, and the second section 66 of the biasable arm 64 is connected to the first section 65 and extends inwards towards the central axis 32. As can be seen, the second section 66 of the biasable arm 64 further comprises first and second arm portions 67, 68 that are angularly connected together to form a lower contact point 69. The lower contact point 69 may substantially face the central axis 32 and the interior of the aperture 30, thereby providing an interface with a medical instrument positioned within the aperture 30. Similar to the upper contact point 57, the lower contact point 69 is axially movable between the extending platform 63 and the central axis 32.

The extending platform 63 may have a radius that substantially matches a radius of the sidewall 40. The first section 65 of the biasable arm 64 may be positioned radially exterior of the extending platform 63 and the sidewall 40. The first section 65 may be provided to allow for the biasable arm 64 to move when the lower contain point 69 is contacted by a medical instrument. However, the first section 65 may also be used to help retain the device 10 within the sterilization platform hole. For example, the first section 65 may be sized larger than the hole within the grommet-holding structure to prevent the device 10 from slipping or moving out of position within the hole. Since the first section 65 and the extending platform 63 are slightly flexible, the device 10 may be inserted into the grommet-holding structure hole by pushing the first section 65 through the grommet-holding structure hole until the sidewall 40 is properly located within the hole. In this position, the larger circular top structure 20 may prevent the device 10 from moving further into the hole.

It is noted that the first section 65 and the circular top structure 20 may be sized to allow for easy insertion and removal of the device 10. Removal of the device 10 may be needed when the device 10 is intended to be disposable on a regular basis, such as after one use or just a few uses. Conventional grommets are not generally intended to be removable or disposable, and therefore may not be sized for convenient removal from the grommet-holding structure. When conventional grommets are removed, it is often a long and labor-intensive process, since their structures are not accommodating for removal. The device 10, on the other hand, may be removed to expose the spaces between the device 10 and the grommet-holding structure, thereby allowing these spaces to be cleaned and sterilized. This may prevent the harboring of bacteria in spaces where sterilant often cannot reach. Accordingly, the device 10 may be considered disposable, in that a new device 10 may be used each time a device 10 is needed. This may assure a higher degree of cleanliness, thereby providing a safer environment for medical instruments.

The upper and lower protruding structures 50, 60 may be constructed from a flexible material, such as silicon, thereby allowing the upper and lower protruding structures 50, 60 to flex and move when contacted by a medical instrument. The overall shape and size of the upper and lower protruding structures 50, 60 may vary according to the design and intended use of the device 10. For example, as is shown in FIGS. 1-2, the upper and lower protruding structures 50, 60 may be positioned to protrude inwards towards the center axis 32, thereby obstructing some of the space of the aperture 30. When a medical instrument is inserted into the aperture 30, the upper and lower protruding structures 50, 60 may be biased towards the sidewall 40. This movement may lessen their obstruction of the aperture 30 and may also place the upper and lower protruding structures 50, 60 in a biased state, where they continually push inwards towards the center axis 32. When the medical instrument is at least partially positioned interior of the upper and lower protruding structures 50, 60, the force exerted by the upper and lower protruding structures 50, 60 on the medical instrument may retain the medical instrument in a substantially stationary position.

The various components of the upper and lower protruding structures 50, 60 may include a variety of variations and changes. For example, the upper protruding structures 50 generally will have a portion that may substantially flex or bend and a portion that does not substantially flex or bend. However, it should be noted that the various portions of the upper protruding structures 50 may include different flexing or bending characteristics, depending on the design of the device 10. Similarly, the different sections of the lower protruding structures 60 may have different abilities to flex and bend. All variations are considered within the scope of the present disclosure.

Any of the components of the device 10, including the structure 20, the aperture 30, the sidewall 40, and the upper and lower protruding structures 50, 60 may have any sizes. For example, a variety of interior and exterior diameters, thicknesses, or other dimensions may be included with the device 10. Similarly, the overall dimensions of the device 10, including the overall thickness and external diameter may have any size. For example, the device 10 may be constructed with different overall sizes to accommodate various types of medical instruments, or various grommet-holding structures. All variations are considered within the scope of the present disclosure.

The device 10 may be a substantially cylindrical structure around the circular top structure 20 and the sidewall 40, all of which may be integrally connected. The upper and lower protruding structures 50, 60 may be integrally formed with the circular top structure 20 and/or the sidewall 40, thereby making the device 10 a substantially unitary structure. Alternatively, various parts or components of the device 10 may be formed separately and permanently or non-permanently affixed together. Commonly, the device 10 may be constructed from a rubber or silicon material that is substantially resistant to degradation from use and from sterilization environments. Within the medical industry, medical instruments are often sterilized in autoclaves, which utilize high temperatures, high pressures, moisture, and/or chemicals to sterilize a medical instrument.

Figure 3:
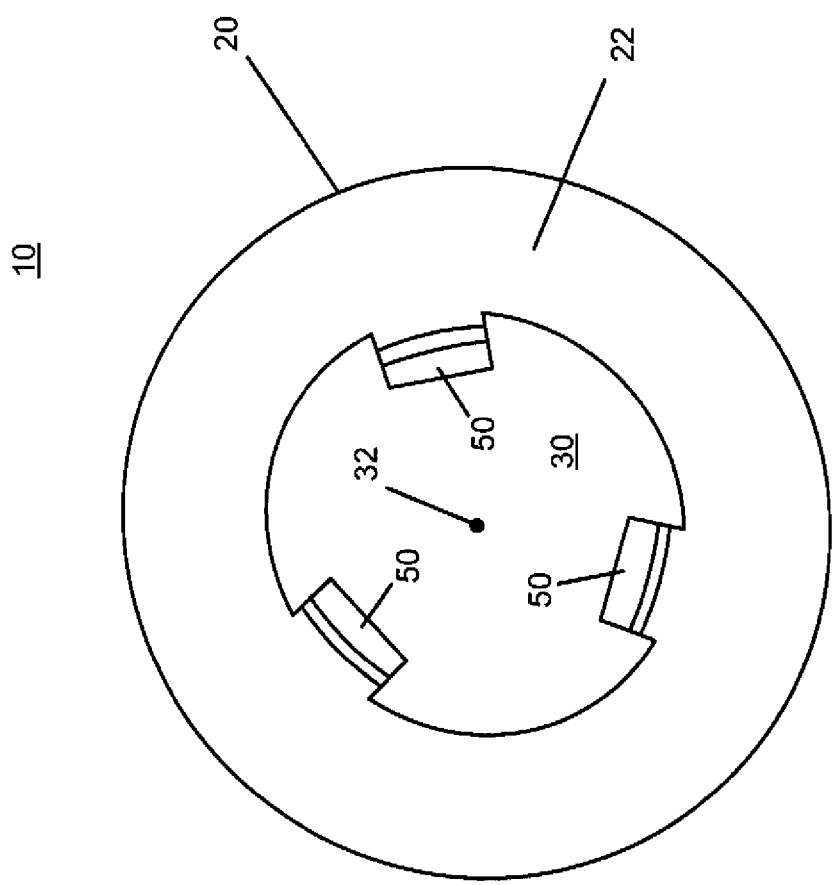
FIG. 3 is a top view illustration of the grommet device, in accordance with the first exemplary embodiment of the present disclosure.

FIG. 3 is a top view illustration of the grommet device 10, in accordance with the first exemplary embodiment of the present disclosure. As is shown, the upper protruding structures 50 may each be integral with the circular top structure 20 and face inwards towards the center axis 32 (illustrated as a point perpendicular to the plane of the paper). At least two upper protruding structures 50 may be included with the device. FIGS. 1-4 illustrate three upper protruding structures 50 with the device 10, but more than three may be included. The overall area of the aperture 30 may be determined relative to the number of upper protruding structures 50 within the device and their respective positions. For example, the greater the shaft diameter of a medical instrument, the greater the upper protruding structures 50 may flex away from the center axis 32, the larger the overall aperture 30 size may be. All variations, configurations and possible designs are considered within the scope of the present disclosure.

Figure 4:
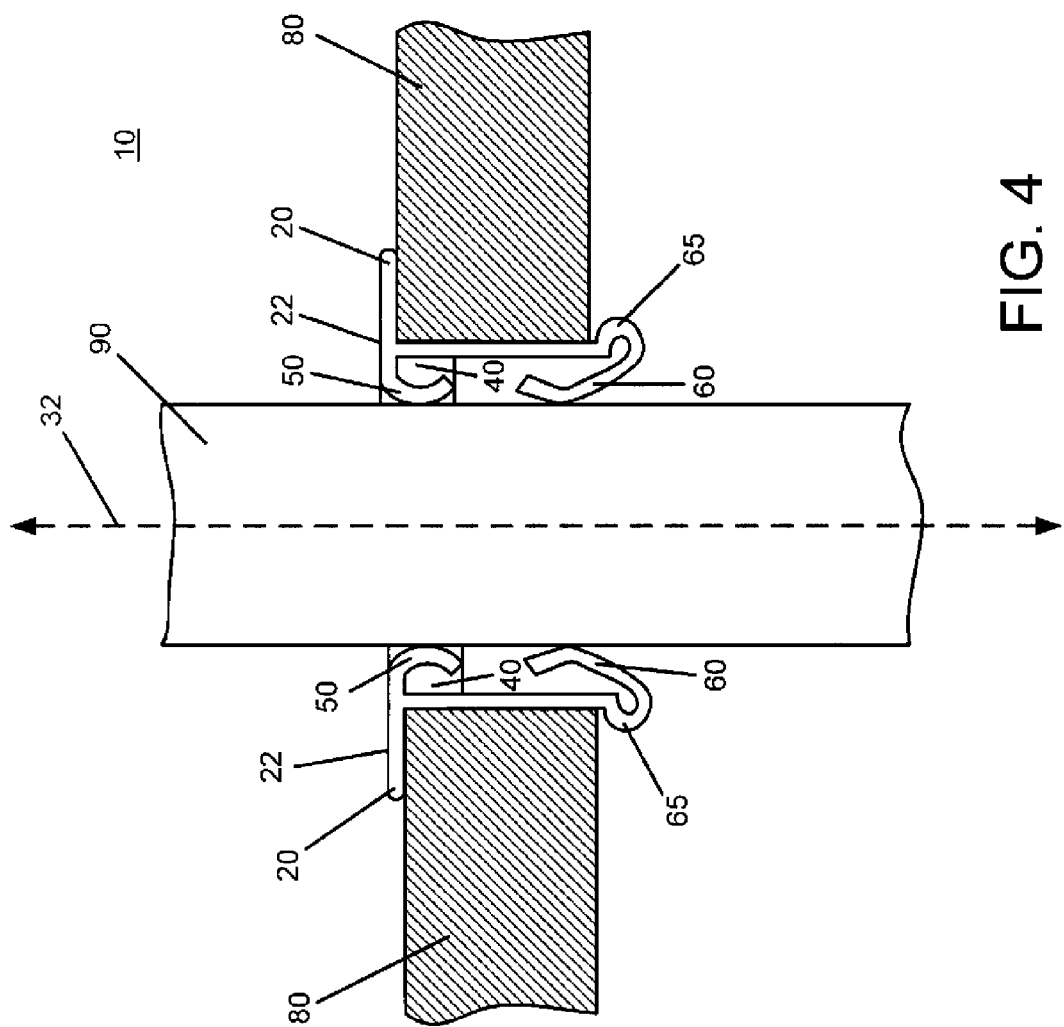
FIG. 4 is a cross-sectional view illustration of the grommet device positioned in use with a grommet-holding structure and medical instrument, in accordance with the first exemplary embodiment of the present disclosure.

FIG. 4 is a cross-sectional view illustration of the grommet device 10 positioned in use with a grommet-holding structure and medical instrument 90, in accordance with the first exemplary embodiment of the present disclosure. The grommet-holding structure 80, which may be any type of sterilization platform, tray, or other structure capable of holding the device 10, is shown with the first section 65 of the device 10 positioned on one side of the grommet-holding structure 80 and the circular top structure 20 positioned on an opposing side. Thus, the device 10 is at least partially positioned within the opening, hole, or aperture within a grommet-holding structure 80. A medical instrument 90 is shown in the in-use position with the device 10.

As is shown, the medical instrument 90, which may be a scalpel, or other tool, biases portions the upper and lower protruding structures 50, 60 away from the center axis 32. Since the upper and lower protruding structures 50, 60 are designed to move towards their original position, i.e., a position where the upper and lower protruding structures 50, 60 are each protruding towards the center axis 32, as discussed relative to FIG. 2, the upper and lower protruding structures 50, 60 may create an inward force on the medical instrument 90. In other words, the natural flex of the flexible protruding structures 60 may subject a force on the medical instrument 90 towards the center axis 32. This force, or combination of forces when the upper and lower protruding structures 50, 60 are used, may successfully retain the medical instrument 90 in a proper position. In this position, the medical instrument 90, device 10, and grommet-holding structure 80 may be easily transported or subjected to a sterilization process without the dislodging of the medical instrument 90 from the device 10, and the device 10 from the grommet-holding structure 80.

Figure 5:
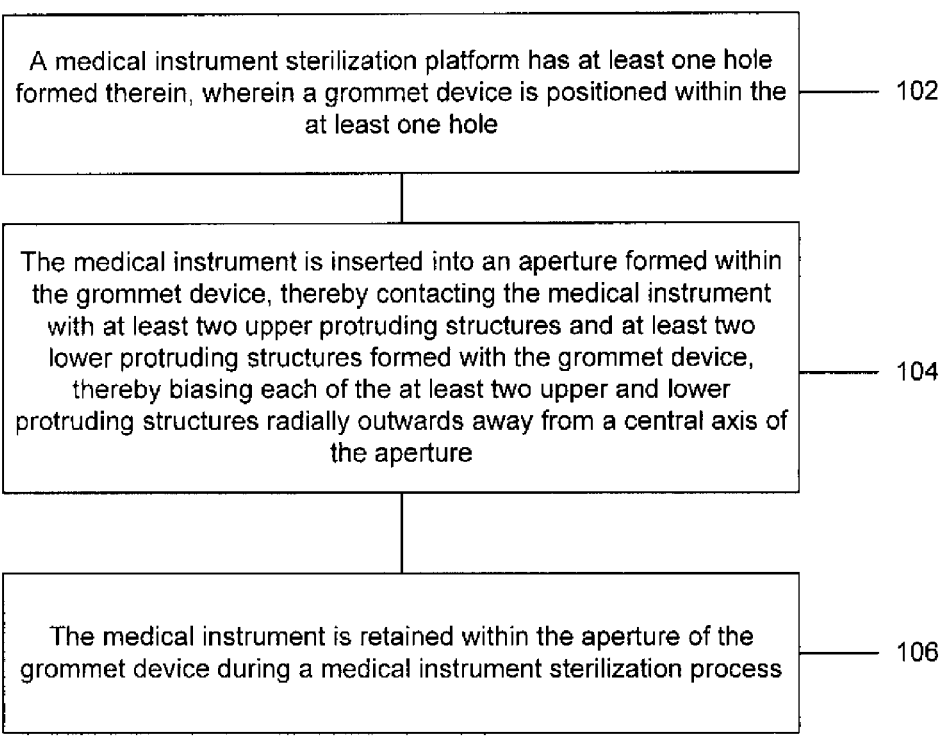
FIG. 5 is a flowchart illustrating a method of constructing a grommet device, in accordance with the first exemplary embodiment of the disclosure.

FIG. 5 is a flowchart 100 illustrating a method of sterilizing a medical instrument, in accordance with a second exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a medical instrument sterilization platform has at least one hole formed therein, wherein a grommet device is positioned within the at least one hole. The medical instrument is inserted into an aperture formed within the grommet device, thereby contacting the medical instrument with at least two upper protruding structures and at least two lower protruding structures formed with the grommet device, thereby biasing each of the at least two upper and lower protruding structures radially outwards away from a central axis of the aperture (block 104). The medical instrument is retained within the aperture of the grommet device during a medical instrument sterilization process (block 106).

The method may include any number of additional steps, processes, or variations thereof, including any of the functions, structures, or disclosures discussed relative to any other embodiment of this disclosure. For example, the method may include the step of retaining the medical instrument within the aperture of the grommet device by frictionally retaining the medical instrument within the aperture. Frictional retention of the medical instrument may be accomplished by exerting a force on the medical instrument with each of the at least two upper protruding structures and at least two lower protruding structures. Once the sterilization process is complete, the medical instrument and the grommet device may be removed from the sterilization platform. The medical instrument may be used within a medical procedure or stored for later use in a medical procedure. The grommet device may be removed and discarded, replaced, or sterilized and reinserted back into the hole of the sterilization platform.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claim.

What is claimed is:

1. A grommet device comprising:
a circular top structure having a top surface, wherein an aperture having a central axis is positioned interior of the top structure;
a sidewall formed around the aperture and connected to the circular top structure, wherein the sidewall is positioned substantially perpendicular from the top surface of the circular top structure;
at least two upper protruding structures connected to the circular top structure at different locations along the circular top structure, wherein each of the at least two upper protruding structures extends into the aperture; and
at least two lower protruding structures extending from the sidewall at different locations along the sidewall, wherein each of the at least two lower protruding structures have a flexing portion extending into the aperture, wherein each the at least two upper protruding structures is substantially radially aligned with the flexing portion of each of the at least two lower protruding structures, respectively.

2. The grommet device of claim 1, wherein the sidewall extends in a substantially perpendicular direction from the circular top structure a first distance terminating at a bottom edge of the sidewall, wherein a lowermost portion of the at least two upper protruding structures is substantially positioned aligned with the bottom edge of the sidewall.

3. The grommet device of claim 1, wherein the at least two upper protruding structures further comprises:
a platform connected to the circular top structure, wherein the platform has an upper surface that is substantially planar with the top surface; and
a biasable arm integral with the platform, wherein the biasable arm angularly extends towards the central axis from the platform.

4. The grommet device of claim 3, wherein the biasable arm further comprises first and second arm portions angularly connected together to form an upper contact point, wherein the upper contact point substantially faces the central axis.

5. The grommet device of claim 4, wherein the upper contact point is axially movable between the sidewall and the central axis.

6. The grommet device of claim 1, wherein the flexing portion of the at least two lower protruding structures further comprises:
an extending platform connected to the sidewall, wherein the extending platform is substantially aligned with the sidewall; and
a biasable arm integral with the platform, wherein a first section of the biasable arm is angularly connected to the extending platform and extends outwards from the central axis, and a second section of the biasable arm is connected to the first section and extends inwards towards the central axis.

7. The grommet device of claim 6, wherein the extending platform has a radius that substantially matches a radius of the sidewall.

8. The grommet device of claim 6, wherein the first section of the biasable arm is positioned radially exterior of the extending platform and the sidewall.

9. The grommet device of claim 6, wherein the second section of the biasable arm further comprises first and second arm portions angularly connected together to form a lower contact point, wherein the lower contact point substantially faces the central axis.

10. The grommet device of claim 9, wherein the lower contact point is axially movable between the extending platform and the central axis.

11. The grommet device of claim 1, wherein the at least two upper protruding structures further comprises:
a platform connected to the circular top structure, wherein the platform has an upper surface that is substantially planar with the top surface; and
a biasable arm integral with the platform, wherein the biasable arm angularly extends towards the central axis from the platform;
wherein the flexing portion of the at least two lower protruding structures further comprises:
an extending platform connected to the sidewall, wherein the extending platform is substantially aligned with the sidewall; and
a biasable arm integral with the platform, wherein a first section of the biasable arm angularly is connected to the extending platform and extends outwards from the central axis, and a second section of the biasable arm is connected to the first section and extends inwards towards the central axis.

12. The grommet device of claim 11, further comprising a medical instrument positioned within the aperture and substantially aligned with the central axis, wherein the medical instrument is contacted by the biasable arm of the at least two upper protruding structures and the second section of the biasable arm of the at least two lower protruding structures.

13. The grommet device of claim 12, wherein when the medical instrument is positioned within the aperture and contacted by the biasable arm of the at least two upper protruding structures and the second section of the biasable arm of the at least two lower protruding structures, the at least two upper protruding structures and the flexing portions of the at least two lower protruding structures are in a biased position, wherein in the biased position, the at least two upper protruding structures and the flexing portions of the at least two lower protruding structures exert a force towards the central axis.

* * * * *